United States Patent [19]

Cherif Cheikh

[11] Patent Number: 5,279,608
[45] Date of Patent: Jan. 18, 1994

[54] OSMOTIC PUMPS

[75] Inventor: Roland Cherif Cheikh, Issy les Moulineaux, France

[73] Assignee: Societe de Conseils de Recherches et d'Applications Scientifiques (S.C.R.A.S.), France

[21] Appl. No.: 802,326

[22] Filed: Dec. 4, 1991

[30] Foreign Application Priority Data

Dec. 18, 1990 [GB] United Kingdom ............... 9027422

[51] Int. Cl.$^5$ ............................................. A61M 5/14
[52] U.S. Cl. .................................. 604/892.1; 604/131; 604/890.1
[58] Field of Search ................. 604/890.1–892.1, 130–133, 140–143, 151, 218; 424/457

[56] References Cited

U.S. PATENT DOCUMENTS

| | | |
|---|---|---|
| 3,604,417 | 9/1971 | Stolzenberg et al. |
| 3,760,984 | 9/1973 | Theeuwes . |
| 3,845,777 | 11/1974 | Gilson . |
| 4,034,756 | 7/1977 | Higuchi et al. . |
| 4,552,561 | 11/1985 | Eckenhoff et al. . |
| 4,838,862 | 6/1989 | Baker et al. . |
| 4,898,582 | 2/1990 | Faste . |
| 4,969,884 | 11/1990 | Yum ................ 604/892.1 |
| 5,062,829 | 11/1991 | Pryor et al. ......... 604/892.1 |
| 5,151,093 | 9/1992 | Theeuwes et al. ..... 604/892.1 |
| 5,169,390 | 12/1992 | Athayde et al. ...... 604/892.1 |

OTHER PUBLICATIONS

S. Rose and J. F. Nelson, "A Continuous Long–Term Injector", Austral. J. Exp. Biol. (1955), 33, pp. 415–420.

Primary Examiner—Randall L. Green
Assistant Examiner—Rob Clarke
Attorney, Agent, or Firm—Lucas & Just

[57] ABSTRACT

An osmotic pump comprises a housing (2) within which is a delivery chamber (5) separated from an osmotic salt chamber (7) by impermeable moveable pressure responsive means such as a piston (6) or a flexible membrane. The osmotic salt chamber (7) is separated from a source of osmotic fluid, e.g. an osmotic fluid chamber (12), by a semipermeable membrane (96,36), optionally mounted in a piston (9,23). A fluid barrier isolates the osmotic salt chamber (7) from the source of osmotic fluid for storage of the pump, and may be inactivated when the pump is to be used. The fluid barrier may be a foil sheet (10), inactivatable by rupture, or a piston and a fluid bypass arrangement (21,23). Activation of the osmotic pump may be effected in some embodiments by loading the discharge chamber (5) with the agent to be delivered and in other embodiments by movement of a plunger (16), under manual control or, if the plunger is pre-biassed, by release of a locking means (18) which holds it in position.

13 Claims, 5 Drawing Sheets

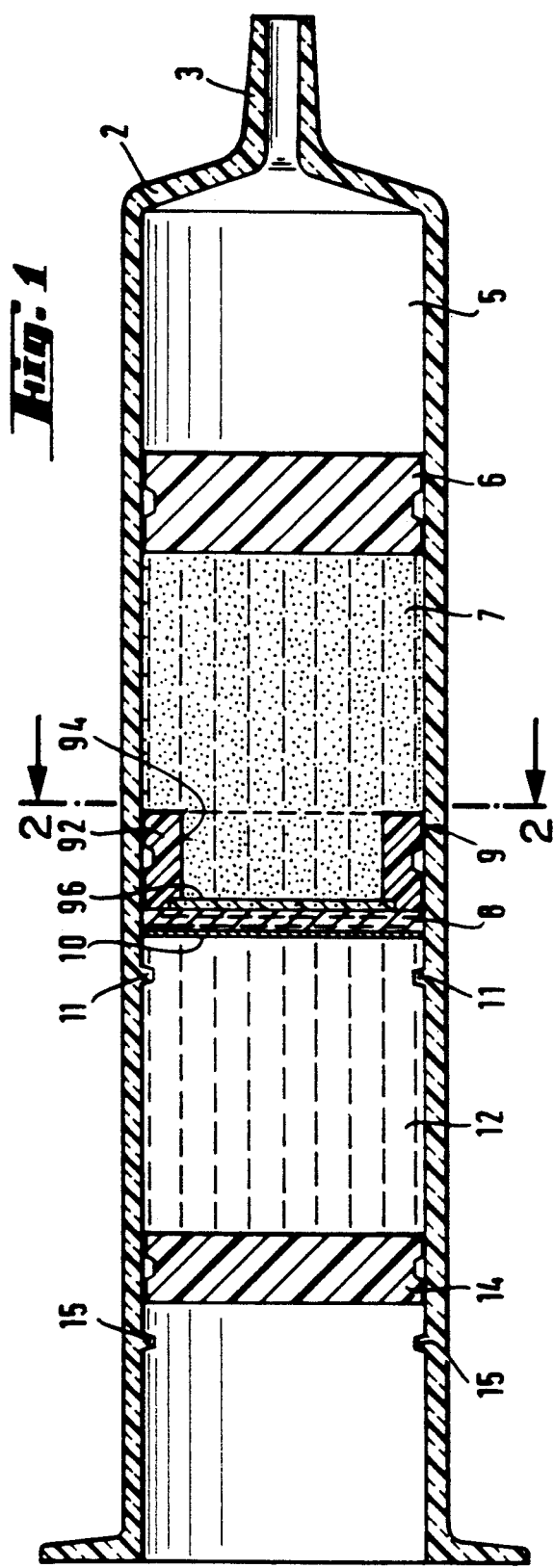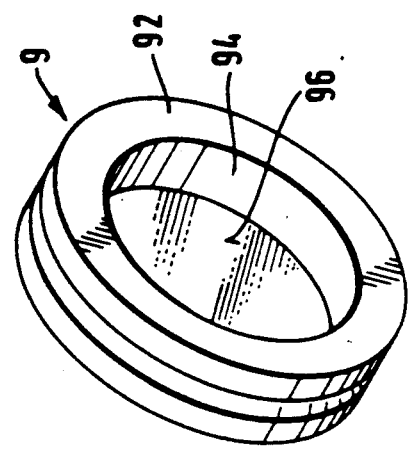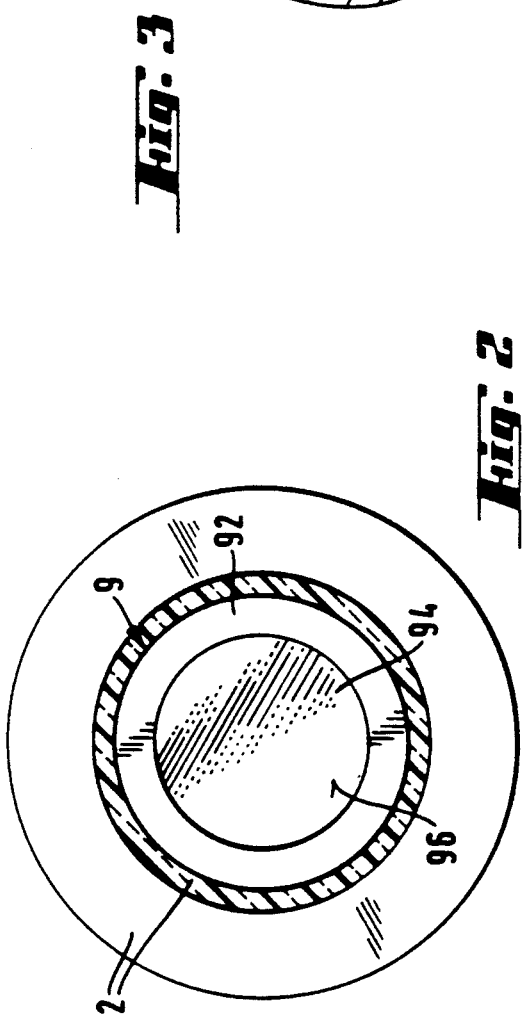

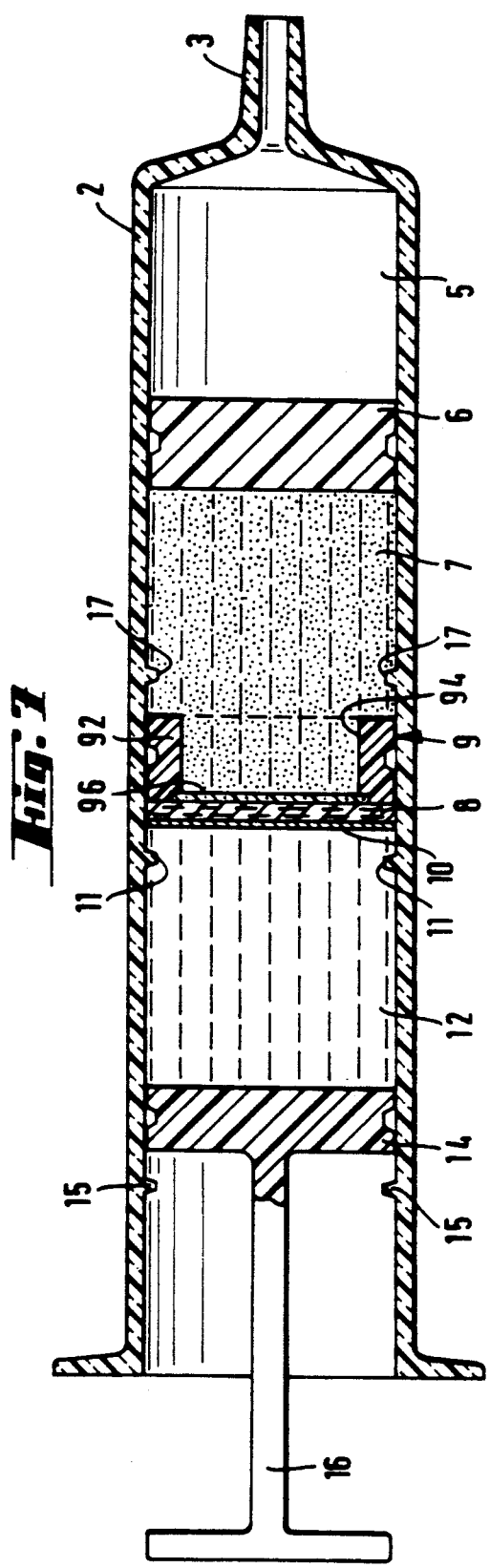
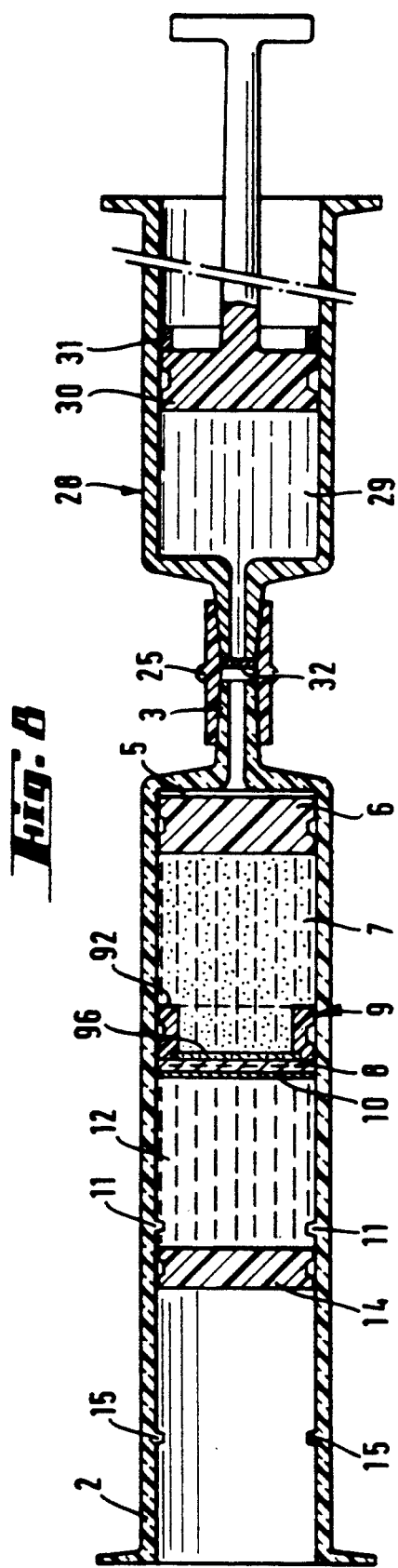

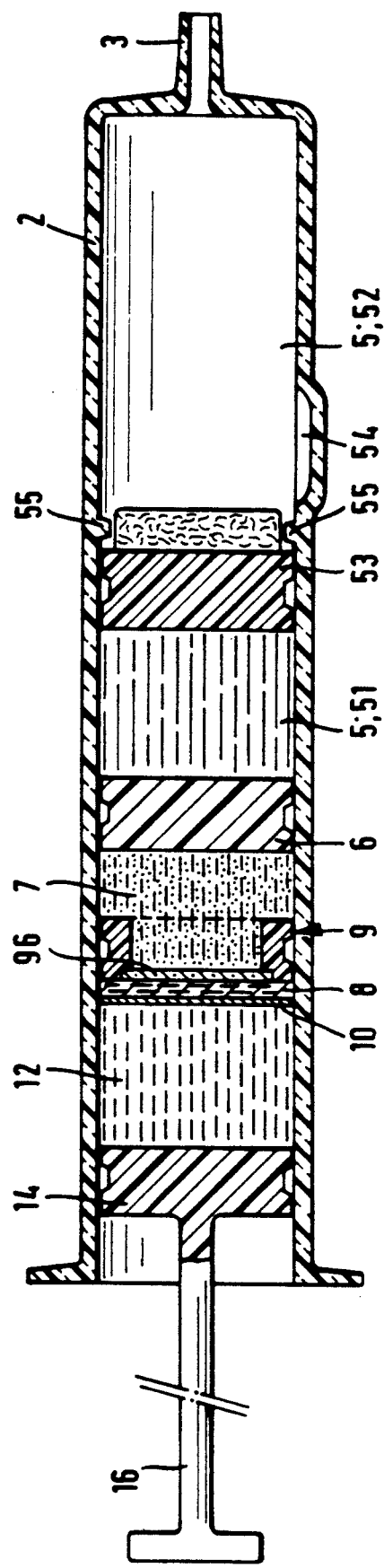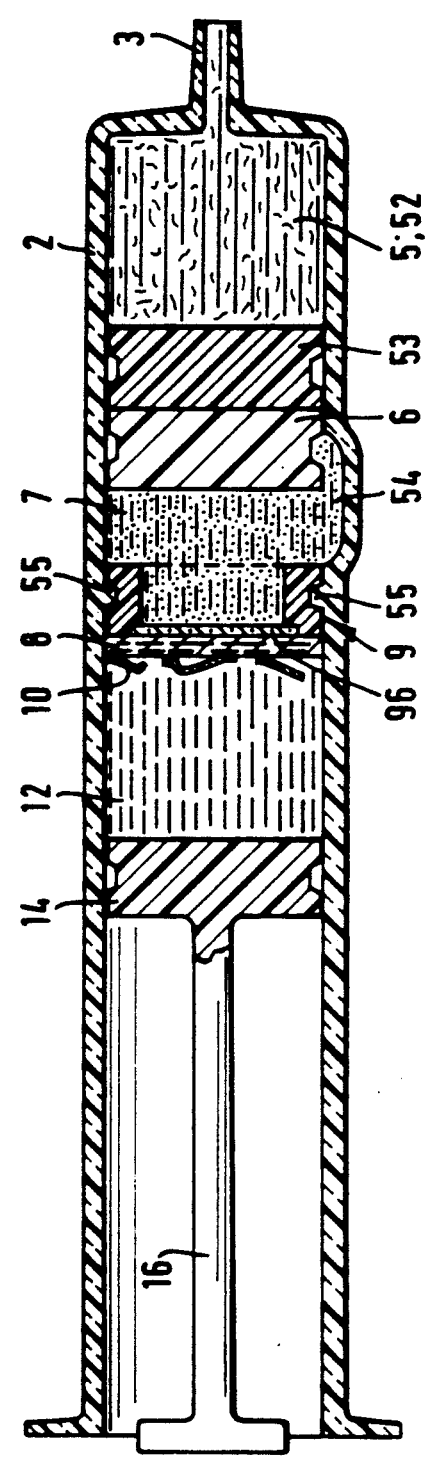

OSMOTIC PUMPS

The invention relates to osmotic pumps capable of delivering a fluid over a prolonged period of time.

Because of their mode of action, dosage requirements, secondary effects, or toxicity, some therapeutic agents require continuous parenteral administration over prolonged periods of time. Traditionally, continuous parenteral delivery has been accomplished with an intravenous drip apparatus. Intravenous drip apparatuses are, however, bulky and fragile, and require immobilization (and frequently hospitalization) of the patient.

The development of new parentally delivered pharmaceutical agents, particularly peptides and peptide derivatives, together with the desire to provide a means of parenteral delivery that does not severely restrict the activity of the recipient, has led to the development of numerous devices for the ambulatory parenteral delivery of pharmaceutical agents. These devices include microcapsules, liposomes, patches, and mechanical pumps.

Mechanical pumps are a particularly favourable means for effecting the parenteral delivery of a fluid over a prolonged period of time. In these devices, a motive force is applied to a liquid, expelling the liquid from the body of the pump. Battery operated motors, inflated balloons, and the vapour pressure of volatile liquids, have all been used to provide the motive force to drive parenteral delivery pumps. Pumps using these methods for the expulsion of a liquid from the pump body suffer from one or more major disadvantages. Chief among these disadvantages are complexity, high cost (which renders single use disposable devices impractical), unreliability, and the inability to deliver small (millilitre) volumes.

Ambulatory infusion devices have also been powered by osmotic pumps, which eliminate many of the disadvantages described above and, in particular, allow for single-use disposable devices. Osmotically driven infusion pumps were first described in Rose and Nelson (1955) Austral. J. Exp. Biol. 33:415–420. A typical Rose-Nelson osmotic pump includes a chamber containing water, a chamber containing salt, and a chamber containing the pharmaceutical agent to be delivered. The water chamber is separated from the salt chamber by a rigid membrane that is permeable to water but not to salt, i.e. a semipermeable membrane. The salt chamber is separated from the chamber containing the pharmaceutical agent by an impermeable moveable partition, typically an impermeable resilient membrane. In operation, water flows through the semipermeable membrane into the salt chamber, increasing the volume of the salt chamber and exerting pressure on the resilient membrane between the salt chamber and the chamber containing the pharmaceutical agent. The volume of the chamber containing the pharmaceutical agent is thereby reduced, expelling the pharmaceutical agent from the pump.

Infusion devices powered by Rose-Nelson osmotic pumps exist in many forms. Improvements and variations in the number and arrangement of the chambers, the moveable impermeable partition between the salt and pharmaceutical agent chambers, the means of loading, and the means of activating the devices are all known. For example, U.S. Pat. Nos. 3760984 and 3845777 describe devices which do not possess osmotic fluid chambers but which imbibe water from outside the pump. In a device described in U.S. Pat. No. 3604417, a moveable piston separates the salt and pharmaceutical agent chambers, and serves to expel the pharmaceutical agent from the pump. U.S. Pat. No. 4552561 describes an infusion device wherein the agent to be delivered is added to the pump and the pump activated separately by the addition of a hydrogel. U.S. Pat. Nos. 4838862 and 4898582 describe osmotic pumps in which the osmotic driving fluid and the drug are loaded into the pump prior to use, and the pump activated by a separate manual manipulation performed at the time of use.

The invention provides an osmotic pump comprising a delivery chamber, an osmotic salt chamber, impermeable moveable pressure responsive means between the delivery chamber and the osmotic salt chamber, a semipermeable membrane between the osmotic salt chamber and a source of osmotic fluid, and a fluid barrier for isolating the source of osmotic fluid from the osmotic salt chamber, the fluid barrier being capable of inactivation when the osmotic pump is to be used.

A pump according to the invention may be supplied with the agent to be dispensed preloaded in the delivery chamber, or with the agent to be dispensed preloaded in a storage chamber from which it is introduced to the delivery chamber immediately prior to use. Such a storage chamber may be detachable from the pump, or may be within the pump between the delivery chamber and the osmotic salt chamber. In some cases, the agent to be dispensed may not be stable as a whole, but may require mixing of two components immediately prior to use. The first component may be a stabilized form of the agent such as a dry, powdered or lyophilized form, and the second component may be a solvent or an injection vehicle. In such a case, one of the first and second components, preferably the first component, may be preloaded in the delivery chamber and the other may be preloaded in a storage chamber (detachable from the pump or within the pump as above described) from which it is introduced to the delivery chamber and mixed with the component therein immediately prior to use. Alternatively, the two components may be preloaded in two separate storage chambers (both detachable from the pump) from which they are introduced together into the delivery chamber immediately prior to use.

The arrangement of parts in a pump according to the invention may be such that, when the agent to be delivered or a component thereof is introduced into the delivery chamber immediately prior to use from a detachable storage chamber (or from two such detachable storage chambers), the increase in pressure in the delivery chamber effects the inactivation of the fluid barrier. Such a pump is described as loading activated. When, however, the agent to be delivered is stored entirely within the delivery chamber or is stored partly in the delivery chamber and partly in a storage chamber within the pump, inactivation of the fluid barrier may be effected by an increase in pressure resulting from movement of a plunger. The plunger may be moved under manual control or may be pre-biassed to move and held by a locking means, release of which allows the plunger to move under the pre-applied bias. Such a pump is described as plunger activated.

The fluid barrier may be a rupturable membrane, such as a sheet of foil, especially aluminium foil. Inactivation of such a fluid barrier is effected by rupturing it when the pump is to be used. The foil sheet would extend across the pump to prevent osmotic fluid from contacting the semipermeable membrane. The fluid barrier may alternatively be a piston moveable, when the osmotic pump is to be used, from a position in which it isolates the source of osmotic fluid from the semipermeable membrane to a position in which it allows fluid communication between the source of osmotic fluid and the semipermeable membrane. Fluid communication would, for example, be through a bypass passage exposed by the movement of the piston.

The semipermeable membrane is preferably moveable. In particular, it may be mounted on a moveable carrying means such as a piston. It may, for example extend across the central aperture of an annular piston. In embodiments in which the fluid barrier is a moveable piston, as described above, the semipermeable membrane may be mounted on the same piston, which would have an impermeable face, an annular skirt dependent from the face and an aperture in the skirt across which the semipermeable membrane extends. In such a case the movement of the piston would be from a position in which the impermeable face isolates the osmotic fluid from the semipermeable membrane to a position in which a bypass passage for the fluid is exposed by the piston and is in register with the semipermeable membrane in the skirt.

The impermeable moveable pressure responsive means may be a piston or a flexible membrane. The source of osmotic fluid may be exterior to the pump, for example being the body fluid of an animal or human, but is preferably contained within the pump in an osmotic fluid chamber. Such an osmotic fluid chamber will be closed at one end by the fluid barrier until use of the pump, and will communicate with the semipermeable membrane following inactivation of the fluid barrier. The osmotic fluid chamber is preferably closed at its other end by moveable pressure responsive means such as a flexible membrane or piston. In embodiments which are activated by movement of a plunger, the plunger is preferably connected to the piston which serves as an end closure to the osmotic fluid chamber.

The osmotic pumps according to the invention may be activated in a single operation. For the loading activated pumps, this operation would be loading the discharge chamber with the agent to be dispensed or with one component of the agent. For the plunger activated pumps, this operation would be depressing the plunger or releasing the locking means thereby allowing the pre-biassed plunger to move. All user initiated pre-installation procedures are collapsed into a single step, greatly simplifying the procedure and eliminating the possibility of the user performing steps out of order, omitting a step (e.g. activating the pump without first loading it), introducing contamination into the material to be delivered, or introducing delay which would lead to the inactivation of a labile agent. Preferably, the plunger activated pumps are provided with a plunger stop to limit the travel of the plunger. The stop may be so placed that the agent to be dispensed is delivered to the exact point of dispensation, e.g. the tip of a sispensing needle or nozzle, avoiding delay (which can be as much as 30 minutes) while sufficient osmotic pressure is built up to ensure dispensation.

The osmotic pumps according to the invention which include an osmotic fluid chamber closed by moveable pressure responsive means do not require wicks, sponges or the like to conduct osmotic fluid to the semipermeable membrane. The pressure responsive end closure means moves in response to flow of osmotic fluid out of the osmotic fluid chamber, progressively decreasing the volume of the osmotic fluid chamber. This prevents the formation of back-pressure or air bubbles and allows the pump to be used in any position. It also allows the pump to respond to any evaporation of osmotic fluid occurring during storage.

Inexpensive versions of the osmotic pumps of the invention can be fabricated from disposable plastics syringes. The housing need contain no seams or other joints which increase the expense of production and the likelihood of leaks.

The invention is illustrated with reference to the drawings. In the different embodiments shown in the drawings, like parts are identified by the same reference numerals. In the drawings:

FIG. 1 is a sectional view of an osmotic pump according to the invention;

FIG. 2 is a sectional view, taken along the line 2—2 of FIG. 1, of a semipermeable piston being a component of the pump of FIG. 1;

FIG. 3 is a perspective view of the semipermeable piston of FIG. 2;

FIG. 7 is a sectional view of yet another osmotic pump according to the invention;

FIG. 8 is a sectional view of a further osmotic pump according to the invention;

FIG. 9a and 9b are sectional views of a yet further osmotic pump according to the invention, FIG. 9a showing the pump in its unactivated condition and FIG. 9b showing the pump in its activated condition;

Figure 4:
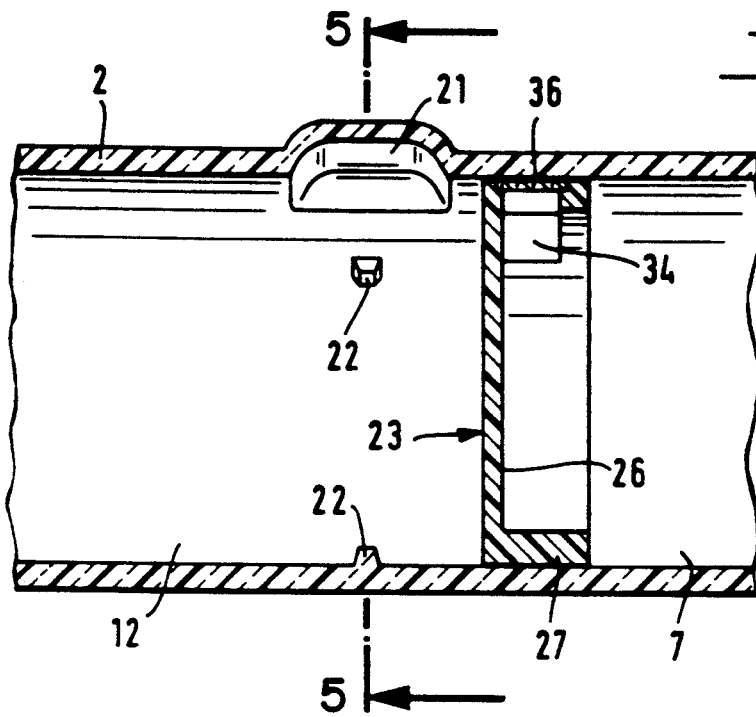
FIG. 4 is a sectional view of a part of another osmotic pump according to the invention.

With reference to FIG. 1 of the drawings, an osmotic pump according to the invention comprises a housing 2, within which are a delivery chamber 5, an osmotic salt chamber 7, an impermeable delivery piston 6 separating the delivery chamber 5 from the osmotic salt chamber 7, an osmotic fluid chamber 12 to serve as a source of osmotic fluid, a semipermeable piston 9 dividing the osmotic salt chamber 7 from the osmotic fluid chamber 12, and a fluid barrier 10 for isolating the osmotic salt chamber 7 from the osmotic fluid chamber 12.

The housing 2 is formed with a charging/delivery nozzle 3 communicating with the delivery chamber 5. The nozzle 3 is of a shape and size to allow easy connection to small diameter catheters or syringes, preferably being compatible with Luer-Lock connection systems. Although a single nozzle 3 is preferred for both charging of and delivery from the delivery chamber 5, separate fittings (not shown) for charging and for delivery could be provided. The delivery chamber 5 may also be provided with a valved port (not shown) for the expulsion of air bubbles.

The semipermeable piston 9, also shown in FIGS. 2 and 3 of the drawings, comprises an annular portion 92 with a central passage 94 across which extends a semipermeable membrane 96. The semipermeable membrane is in contact with a wick 8. Stops 11 are provided to limit the travel of the semipermeable piston 9 in the direction away from the nozzle 3. The osmotic fluid chamber 12 is closed by an end piston 14. Stops 15 are provided to limit the travel of the end piston 14 in the direction away from the nozzle 3.

The housing 2 may be machined or moulded from a suitable heat resistant, chemically inert, sterilizable, rigid material, e.g. polyvinylchloride, polycarbonate, medium or high density polyethylene, or stainless steel. The housing 2 may be transparent to allow the user to monitor the status of the drug or of the osmotic fluid. In particular, the housing 2 can be fabricated from the barrel of a disposable plastics syringe by simple and inexpensive modifications, such as thermal melting of the barrel to form the piston stops 11 and 15.

The pistons 6 and 14 can be fabricated from any materials which are impervious to the fluids and other substances used with the pump and which give a good seal between the piston and the housing 2. Plungers of disposable plastics syringes are suitable for use as the pistons 6 and 14 if the housing 2 is made from such a disposable plastics syringe as above described, or if the housing has an inside diameter equal to the inside diameter of the syringes from which the plunges are taken.

The semipermeable piston 9 is similar to the pistons 6 and 14 except that it is provided with the central passage 94. The semipermeable membrane 96 extending across the passage 94 can be fabricated from one of the cellulose esters or ethers, e.g. cellulose acetate or cellulose butyrate.

The fluid barrier 10 is fabricated from a material which is impermeable to the osmotic fluid and which is easily reptured by movement of the semipermeable piston 9, e.g. aluminium foil.

Osmotic salts suitable for use in the osmotic salt chamber 7 include sodium chloride, potassium chloride, magnesium sulphate and sodium sulphate. The preferred osmotic fluid for use in the osmotic fluid chamber 12 is water, though any combination of salt, solvent, and semipermeable membrane that can generate sufficient osmotic pressure can be used. Parameters important in the choice of osmotic salts and fluids, and the preferred volumes thereof, are discussed in U.S. Pat. Specifications Nos. 4838862 and 4034756.

The wick 8 can be fabricated from filter paper or any porous material capable of absorbing and conducting the osmotic fluid. The wick 8 is optional, serving in some embodiments to keep the osmotic fluid in contact with the semipermeable membrane 96. In the instant embodiment, as more fully described hereinbelow, as the volume of the osmotic fluid chamber 12 decreases, the end piston 14 moves towards the nozzle 3, preventing the formation of a bubble in the osmotic fluid chamber 12 and acting to keep the osmotic fluid in contact with the semipermeable membrane 96, eliminating or lessening the need for a wick 8. This movement of the end piston 14 also helps to prevent the build-up of backpressure in the osmotic fluid chamber 12.

In operation, a liquid to be delivered is introduced, under pressure, into the delivery chamber 5 (e.g. by a disposable syringe connected to the nozzle 3), forcing the delivery piston 6, the salt in the osmotic salt chamber 7 and the semipermeable piston 9 towards the fluid barrier 10, causing the latter to rupture. Rupture is effected either by the pressure of the semipermeable piston 9, or by an element (not shown), the shape of which is such as to prevent damage to the semipermeable membrane 96. The travel of the semipermeable piston 9 is arrested by the stops 11, which are disposed to allow the minimum displacement of the semipermeable piston 9 consistent with rupture of the fluid barrier 10, preferably about 1 to 2 mm. The travel of the end piston 14 (in the direction away from the nozzle 3) is controlled and limited by the travel of the semipermeable piston 9. As an extra safety precaution, the optional piston stops 15 arrest the travel of the end piston 14 after the fluid barrier 10 has been broken.

The rupture of the fluid barrier 10 allows osmotic fluid to pass from the osmotic fluid chamber 12, through the wick 8 and the semipermeable membrane 96, into the osmotic salt chamber 7, where it contacts the osmotic salt. Osmotic force thereby generated drives the delivery piston 6 towards the nozzle 3, reducing the volume of the delivery chamber 5 and forcing the liquid in the delivery chamber 5 through the nozzle 3 to the delivery site. As the volume of osmotic fluid in the osmotic fluid chamber 12 decreases, the end piston 14 is displaced from its initial position to decrease the volume of the osmotic fluid chamber 12 and thus prevents the formation of a vacuum in the osmotic fluid chamber 12.

The delivery piston 6 is sensitive to changes in the volume of the chambers (5,7) on either side. When the delivery chamber 5 is filled with a liquid, the delivery piston 6 responds to an increase in the volume of the delivery chamber 5 by forcing the semipermeable piston 9 against the fluid barrier 10, thereby rupturing it. Later, the delivery piston 6 responds to an increase in the volume of the osmotic salt chamber 7 (due to the inflow of osmotic fluid) by decreasing the volume of the delivery chamber 5 and thereby expelling its contents.

The osmotic pump is suitable for the delivery of any agent or combination of agents that would normally be administered parenterally, including natural, synthetic, or recombinant peptide or protein drugs, analgesics, or antidotes to venoms or to chemical or biological poisons. The agents can be dissolved in or mixed with any appropriate injection vehicle and introduced in liquid form into the delivery chamber 5.

Unstable agents can be supplied in stable form, e.g. as a lyophilized powder, which is mixed with the appropriate injection vehicle prior to introduction into the delivery chamber 5. Mixing of the agent with its injection vehicle can be simplified by supplying the agent and injection vehicle in a two-compartment syringe e.g. a TURM syringe. One compartment of the two-compartment syringe holds the agent to be delivered and the other compartment holds the injection vehicle. The contents of the two compartments are separated from contact with each other until the plunger of the two-compartment syringe is depressed. Upon depression of the plunger, the contents of the compartments mix. The resulting mixture is then forced into the delivery chamber of the osmotic pump, charging and activating it. Alternatively, the osmotic pump can be supplied with a stable form of the agent preloaded in the delivery chamber. The user forces the injection vehicle into the delivery chamber, e.g. with a syringe which mates with the nozzle 3, thereby simultaneously mixing the agent with its injection vehicle and charging and activating the osmotic pump.

Various components of the osmotic pump above described may be replaced by other components of similar function but different construction. For example, the delivery piston 6 can be replaced by another pressure responsive mechanism such as a flexible impermeable membrane or diaphragm. Any other mechanism, which is impermeable to the salts and fluids used, and that (a)

can translate an increase in the volume of the delivery chamber 5 into movement or pressure that directly or indirectly triggers flow of osmotic fluid into the osmotic salt chamber 7 and (b) can translate an increase in the volume of the osmotic salt chamber 7 into a decrease in the volume of the delivery chamber 5, can be used. The end piston 14 can also be replaced by another pressure responsive mechanism such as a flexible impermeable membrane or diaphragm. Flexible membranes impermeable to the salts, fluids, and agents used with the osmotic pump can be fabricated from a wide range of materials known to those skilled in the art, e.g. from latex rubber, polyisoprene, butyl rubber, nitrite rubber, or copolymers of styrene/butadiene. If the osmotic pump is to be stored for long periods of time, the membrane may be faced with a thin layer of aluminium foil to prevent degradation by other components or contents of the device.

Figure 5:
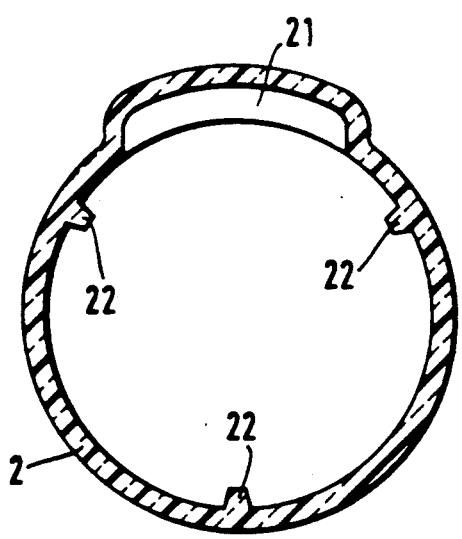
FIG. 5 is a sectional view taken along the line 5—5 of FIG. 4.
Figure 6:
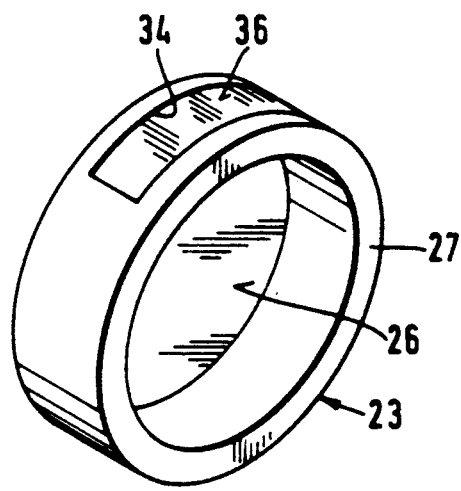
FIG. 6 is a perspective view of a semipermeable piston being a component of the pump of FIG. 4.

The fluid barrier 10 is not restricted to rupturable diaphragms or membranes but may be any mechanism which (a) prevents the flow of osmotic fluid into the osmotic salt chamber 7 prior to an increase in the volume of the delivery chamber 5 and (b) responds to a pressure or movement created directly or indirectly by an increase in the volume of the delivery chamber 5 by allowing osmotic fluid to flow into the osmotic salt chamber 7, thus triggering activation. FIGS. 4 to 6 depict an alternative fluid barrier. In this embodiment, the semipermeable piston 9, wick 8, fluid barrier 10 and piston stops 11 have been removed. The housing 2 has been reshaped to include a fluid passage 21, and a semipermeable piston 23 has been included as have piston stops 22. The semipermeable piston 23 has an impermeable face 26 with a dependent annular skirt 27. In the skirt 27 is an aperture 34 across which extends a semipermeable membrane 36.

Prior to an increase in the volume of the delivery chamber 5, the semipermeable piston 23 is positioned as shown in FIG. 4 so as to prevent the flow of osmotic fluid from the osmotic fluid chamber 12 into the osmotic salt chamber 7. Upon an increase in the volume of the delivery chamber 5, the semipermeable piston 23 is displaced, coming to rest against the stops 22, in a position that allows osmotic fluid to flow from the osmotic fluid chamber 12 through the fluid passage 21 and the semipermeable membrane 36 into the osmotic salt chamber 7, thereby activating the pump.

The osmotic pumps described with reference to FIGS. 1 to 6 of the drawings are loading-activated. This feature is not essential, as will now be described with reference to FIG. 7 of the drawings. The embodiment here shown in similar to that described with reference to FIGS. 1 to 3 of the drawings, but is supplied with the agent to be injected preloaded in the delivery chamber 5. The end piston 14 is attached to a plunger 16. Prior to use, the loaded device can be stored at a temperature which preserves the stability and activity of the agent.

The pump is activated by the application of pressure to the plunger 16, causing the end piston 14 to travel towards the fluid barrier 10, rupturing it and allowing osmotic fluid to pass from the osmotic fluid chamber 12 through the semipermeable membrane 96 and into the osmotic salt chamber 7. Forward stops 17 are provided to arrest the travel of the semipermeable piston 9 and prevent premature discharge of the contents of the delivery chamber 5. As osmotic fluid enters the osmotic salt chamber 7, increasing the volume thereof, the delivery piston 6 is displaced towards the nozzle 3, expelling the contents of the delivery chamber 5. Expansion of the osmotic salt chamber 7 exerts pressure on to semipermeable piston 9 but its travel towards the stops 11 is arrested by the stops 11 or, optionally, by a locking system at the forward stops 17 which captures and immobilizes the semipermeable piston 9.

The end piston 14 can inactivate, e.g. rupture the fluid barrier 10 indirectly, by exerting pressure on osmotic fluid in the osmotic fluid chamber 12. A breaking means (not shown) can be placed between the fluid barrier 10 and the semipermeable piston 9, the shape of the breaking means being such as to prevent damage to the semipermeable membrane 96, to assist in rupture of the fluid barrier 10. Optionally, the fluid barrier 10 can be broken by direct contact, e.g. a projection (not shown) from the end piston 14 could pierce the fluid barrier 10 when the end piston 14 is moved towards the fluid barrier 10. Preferably, this projection does not prevent travel of the end piston 14 during operation of the pump. In the latter embodiment, piston stops (not shown) would be provided to limit the travel of the end piston 14 to prevent damage to the semipermeable membrane 96. To prevent the plunger 16 and end piston 14 from being pulled out of the housing 2 while the pump is in use, the length of the plunger 16 is chosen to minimize its protrusion beyond the housing 2. Alternatively, or in addition, a guard (not shown) may be attached to the end of the housing 2 remote from the nozzle 3 to prevent undesired movement of the plunger 16.

In an alternative embodiment, the semipermeable piston 9 can be replaced by a semipermeable membrane (not shown) fixed immovably to the inside wall of the housing 2, eliminating the need for the stops 11 and 17.

In another alternative embodiment, the semipermeable piston 9, wick 8, fluid barrier 10 and piston stops 11 can be replaced by the fluid passage 21, piston stops 22 and semipermeable piston 23 as described with reference to FIGS. 4 to 6 of the drawings, but preferably modified so that the semipermeable piston 23 is displaced towards the nozzle 3 during activation.

The osmotic pumps of the invention may be supplied with a detachable storage chamber, as shown in FIG. 8 of the drawings. The left hand side of FIG. 8 shows an osmotic pump as described in FIG. 1. This is connected by a connector 25 to a storage chamber unit 28. The storage chamber unit 28 includes a storage chamber 29, a piston and plunger assembly 30, stops 31 and, optionally, a septum 32. In use, the osmotic pump is coupled by the connector 25 to the storage chamber unit 28. The plunger 30 is depressed, breaking the septum 32, forcing the contents of the storage chamber 29 through the connector 25 and into the delivery chamber 5 of the osmotic pump, thereby loading and activating the osmotic pump. The stops 31 limit the ability of the piston and plunger assembly 30 to travel in the wrong direction. This embodiment is particularly useful when the agent to be administered is to be mixed with a second agent just prior to delivery. For example, the embodiment shown in FIG. 8 can be supplied with a dry or otherwise stable form of agent in the delivery chamber 5 and a second agent, e.g. a solvent or injection vehicle, in the storage chamber 29. The plunger 30 is depressed forcing the contents of the storage chamber 29 into the delivery chamber 5 thereby mixing the contents of the storage chamber 29 with the contents of the delivery chamber 5 and loading and activating the osmotic pump. The storage chamber unit 28 is removed prior to use. The storage chamber unit 28 can be fabricated from a plastics syringe and the connector 25 can be fabricated from widely available luer-type connectors.

FIGS. 9a and 9b show another embodiment of an osmotic pump, one that is particularly useful when a first agent is to be mixed with a second agent just prior to delivery. FIG. 9a shows the pump before activation and FIG. 9b shows the pump after activation. The pump is activated by depressing the plunger 16.

The pump in FIGS. 9a and 9b is essentially a combination of the pump shown in FIG. 7 and a two chamber syringe, e.g. a TURM syringe. However, the delivery chamber 5 has been replaced by first and second storage chambers 51 and 52 respectively, separated by a chamber separation piston 53. A fluid passage 54 is formed in the housing 2. In the inactivated condition shown in FIG. 9a, the fluid passage is between the nozzle 3 and the piston 53, so that there is no communication between the chambers 51 and 52. The first storage chamber 51 contains a first agent to be delivered, e.g. an injection vehicle, while the second storage chamber contains a second agent to be delivered, e.g. a lyophilized, powdered or liquid agent, the first and second agents being intended to be mixed prior to delivery and delivered together.

As previously indicated, the pump is activated by depressing the plunger 16, which ruptures the fluid barrier 10 and displaces the osmotic fluid in osmotic fluid chamber 12, the semipermeable piston 9, the osmotic salt in the osmotic salt chamber 7, the delivery piston 6, the first agent to be delivered and the chamber separating piston 53, all towards the nozzle 3. As this displacement proceeds, the chamber separation piston 53 passes over the fluid passage 54 and the first agent to be delivered flows from the first storage chamber 51 through the fluid passage 54 and into the second storage chamber 52, where it mixes with the second agent to be delivered. Pressure on the plunger 16 is maintained, forcing essentially all of the first agent to be delivered into the second storage chamber 52 and reducing the volume of the first storage chamber 51 to essentially zero. Pressure on plunger 16 is maintained until the semipermeable piston 9 engages stops 55, as shown in FIG. 9b. Once engaged, the stops 55 prevent the travel of the semipermeable piston 9 in either direction. In this position, the pump is activated. The first and second agents to be delivered are both disposed in the second storage chamber 52, which acts as the delivery chamber 5, with the delivery piston 6 and chamber separation piston 53 acting together as the delivery piston. Osmotic fluid flows through the semipermeable piston 9 into the osmotic salt chamber 7, forcing the delivery piston (6,53) towards the nozzle 3 and expelling the contents of the delivery chamber (52,5).

Figure 10A:
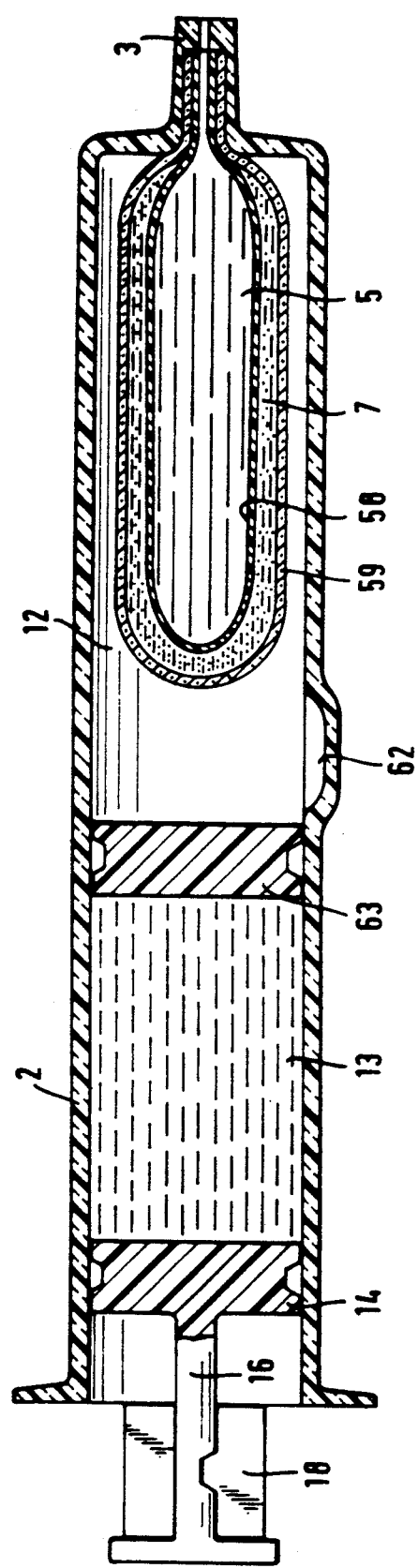
FIGS. 10a and 10b are sectional views of a still further osmotic pump according to the invention, FIG. 10a showing the pump in its unactivated condition and FIG. 10b showing the pump in its activated condition.
Figure 10B:
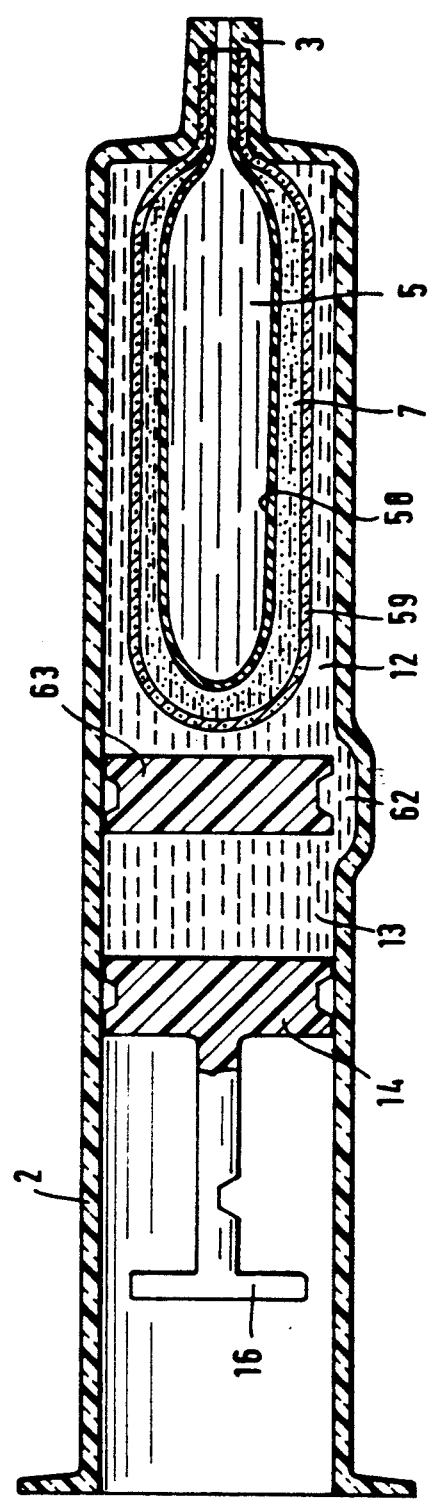

FIGS. 10a and 10b show a further embodiment of an osmotic pump. This embodiment can be manufactured from a two compartment syringe, e.g. a TURM syringe. FIG. 10a shows the pump before activation and FIG. 10b shows the pump after activation. The pump includes a housing 2 made from a TURM syringe, a nozzle 3, a delivery chamber 5, a flexible impermeable membrane 58, an osmotic salt chamber 7 within which is an osmotic salt, a semipermeable membrane 59 (preferably rigid), a fluid passage 62, a separation piston 63, an osmotic fluid chamber 12, an osmotic fluid storage chamber 13, an end piston 14, a plunger 16, and a locking means 18 for the plunger 16. Before activation, the osmotic fluid chamber 12 is empty and preferably under vacuum. Activation consists of removing the locking means 18 which allows the vacuum in the osmotic fluid chamber 12 to draw the separation piston 63 and the end piston 14 towards the nozzle 3. When separation piston 63 reaches the fluid passage 62, osmotic fluid flows from the osmotic fluid storage chamber 13 into the osmotic fluid chamber 12 and into contact with the semipermeable membrane 59. As osmotic fluid flows through the semipermeable membrane 59 and into the osmotic salt chamber 7, the volume of the delivery chamber 5 is decreased and the contents of the delivery chamber 5 are expelled.

I claim:

1. An osmotic syringe comprising a tubular housing with a delivery nozzle at one end thereof, a delivery chamber in said tubular housing adjacent said delivery nozzle, said delivery chamber having delivery material therein, an osmotic salt chamber in said tubular housing adjacent said delivery chamber and remote from said delivery nozzle, said osmotic salt chamber having osmotic salt therein, said osmotic salt chamber being isolated from said delivery chamber by a first movable piston, said first movable piston having an outside diameter which is the same as the inside diameter of the said tubular housing and said first movable piston being longitudinally displaceable in said tubular housing, an osmotic fluid chamber in said tubular housing adjacent said osmotic salt chamber and remote from said delivery chamber, said osmotic fluid chamber having osmotic fluid therein, said osmotic fluid chamber being isolated from said osmotic salt chamber by a semipermeable membrane, said semipermeable membrane being permeable to said osmotic fluid but being impermeable to said osmotic salt, a fluid barrier positioned between said semipermeable membrane and said osmotic fluid chamber, said fluid barrier being capable of inactivation, a second movable piston in said tubular housing at the end of said osmotic fluid chamber remote from said fluid barrier, said second movable piston and said fluid barrier being the ends of the said osmotic fluid chamber in the said tubular housing, said second movable piston having an outside diameter which is the same as the inside diameter of the said tubular housing and said second movable piston being longitudinally displaceable in said tubular housing, and wherein displacement of said second movable piston in longitudinal direction towards said delivery nozzle is capable of inactivating said fluid barrier, whereby, when said fluid barrier is inactivated, osmotic fluid in said osmotic fluid chamber flows through said semipermeable membrane and into said osmotic salt chamber and combines with osmotic salt in said osmotic salt chamber thereby generating osmotic pressure, said osmotic pressure causing said first movable piston to displace longitudinally toward said delivery nozzle, thereby decreasing the size of the delivery chamber and forcing the delivery material out of the delivery chamber through the said delivery nozzle.

2. An osmotic syringe according to claim 1 in which the fluid barrier comprises a sheet of foil, the foil being ruptured when the osmotic syringe is to be used.

3. An osmotic syringe according to claim 1 further comprising an annular piston having a central passage therethrough and in which the semipermeable membrane extends across the central passage of an annular piston.

4. An osmotic syringe according to claim 1 in which the fluid barrier comprises a piston moveable, when the osmotic pump is to be used, from a position in which it isolates the source of osmotic fluid from the semipermeable membrane to a position in which it allows fluid communication between the source of osmotic fluid and the semipermeable membrane.

5. An osmotic syringe according to claim 4 in which the piston comprises an impermeable face, an annular skirt dependent from the face and an aperture in the skirt and in which the semipermeable membrane extends across the aperture.

6. An osmotic syringe according to claim 5 further comprising a bypass passage and in which the movement of the piston brings the semipermeable membrane into register with the bypass passage.

7. An osmotic syringe according to claim 1 further comprising a storage chamber for storing an agent to be delivered by the pump or a part of such an agent.

8. An osmotic syringe according to claim 7 in which the storage chamber is detachable.

9. An osmotic syringe according to claim 7 in which the storage chamber is between the osmotic salt chamber and the delivery chamber and the contents of the storage chamber are introduced into the delivery chamber when the osmotic syringe is to be used.

10. An osmotic syringe according to claim 1 which is activated by the loading of the delivery chamber with an agent to be delivered by the pump or with a part of such an agent.

11. An osmotic syringe according to claim 1 further comprising a plunger connected to the said second movable piston.

12. An osmotic syringe according to claim 11 further comprising locking means for the plunger and in which the plunger is biassed to move upon release of the locking means.

13. An osmotic syringe according to claim 11 in which the movement of the plunger is manually controlled.

* * * * *